United States Patent [19]

Ferlic et al.

[11] Patent Number: 4,901,335
[45] Date of Patent: Feb. 13, 1990

[54] MAMMOGRAPHY APPARATUS

[76] Inventors: Daniel J. Ferlic, 406 Birchwood Ave., White Bear Lake, Minn. 55110; Frank T. Kotula, 15345 70th Pl. North, Maple Grove, Minn. 55369; Kurt Amplatz, 10 Evergreen St., North Oaks, Minn. 55110

[21] Appl. No.: 266,798

[22] Filed: Nov. 3, 1988

[51] Int. Cl.$^4$ ................................................. A61B 6/04
[52] U.S. Cl. ........................................ 378/37; 378/155
[58] Field of Search ........................... 378/154, 155, 37

[56] References Cited

U.S. PATENT DOCUMENTS

| | | |
|---|---|---|
| 1,164,987 | 12/1915 | Bucky . |
| 1,208,474 | 12/1916 | Caldwell . |
| 1,556,217 | 10/1925 | Hamilton . |
| 1,592,279 | 7/1926 | Lechenger . |
| 1,768,769 | 7/1930 | Kelley . |
| 2,511,853 | 6/1950 | Kaiser ................................. 250/62 |
| 3,578,971 | 5/1971 | Lasky ................................. 250/50 |
| 4,020,347 | 4/1977 | Geluk ................................. 250/361 |
| 4,096,391 | 6/1978 | Barnes ............................... 250/505 |
| 4,097,748 | 6/1978 | Monvoisin .......................... 250/505 |
| 4,340,818 | 7/1982 | Barnes ............................... 378/155 |
| 4,563,768 | 1/1986 | Read et al. .......................... 378/37 |
| 4,731,806 | 3/1988 | Takahata ............................ 378/155 |
| 4,759,045 | 7/1988 | Lasky ................................. 378/37 |

OTHER PUBLICATIONS

"Medical Radiography and Photography", a journal published by the Eastman Kodak Company, vol. 62, No. 2, 1986.

Primary Examiner—Craig E. Church
Attorney, Agent, or Firm—Kinney & Lange

[57] ABSTRACT

A mammography apparatus with a cylindrical section, reciprocating slot grid centered on an axis through a source of x-ray radiation. The slot grid includes a plurality of x-ray radiation absorbing lamellae disposed parallel to and aligned radially from the axis. Adjacent pairs of lamellae define air spaced gaps between the members of the pair. The ratio of the height of each of an adjacent pair of lamellae to the width of the respective defined gap being at least 7:1. The slot grid is set in a travel centered on the axis through the x-ray source. The x-ray source is provided with a predetermined staggered turn on and turn off circuit preventing interspace density artifacts.

12 Claims, 8 Drawing Sheets

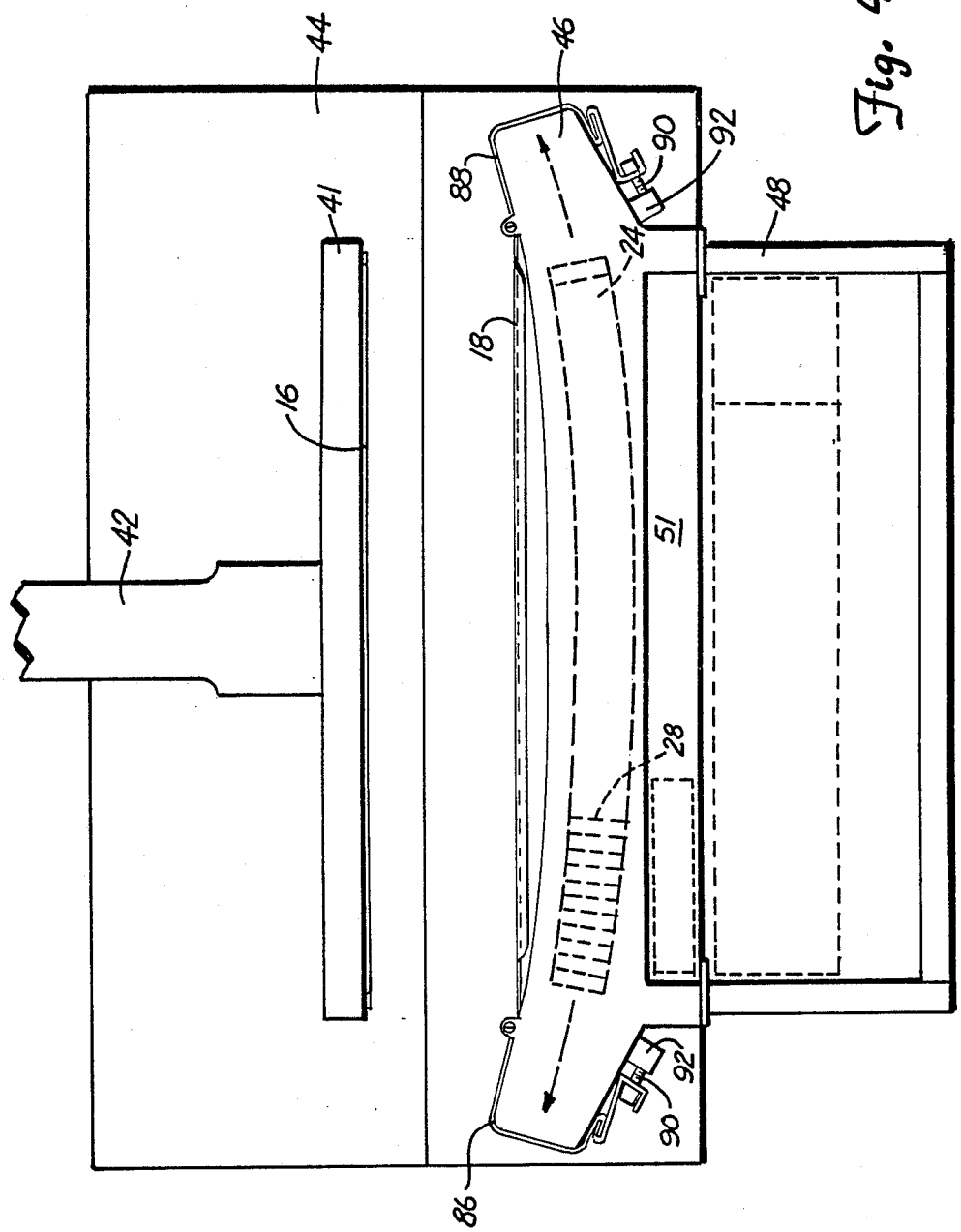

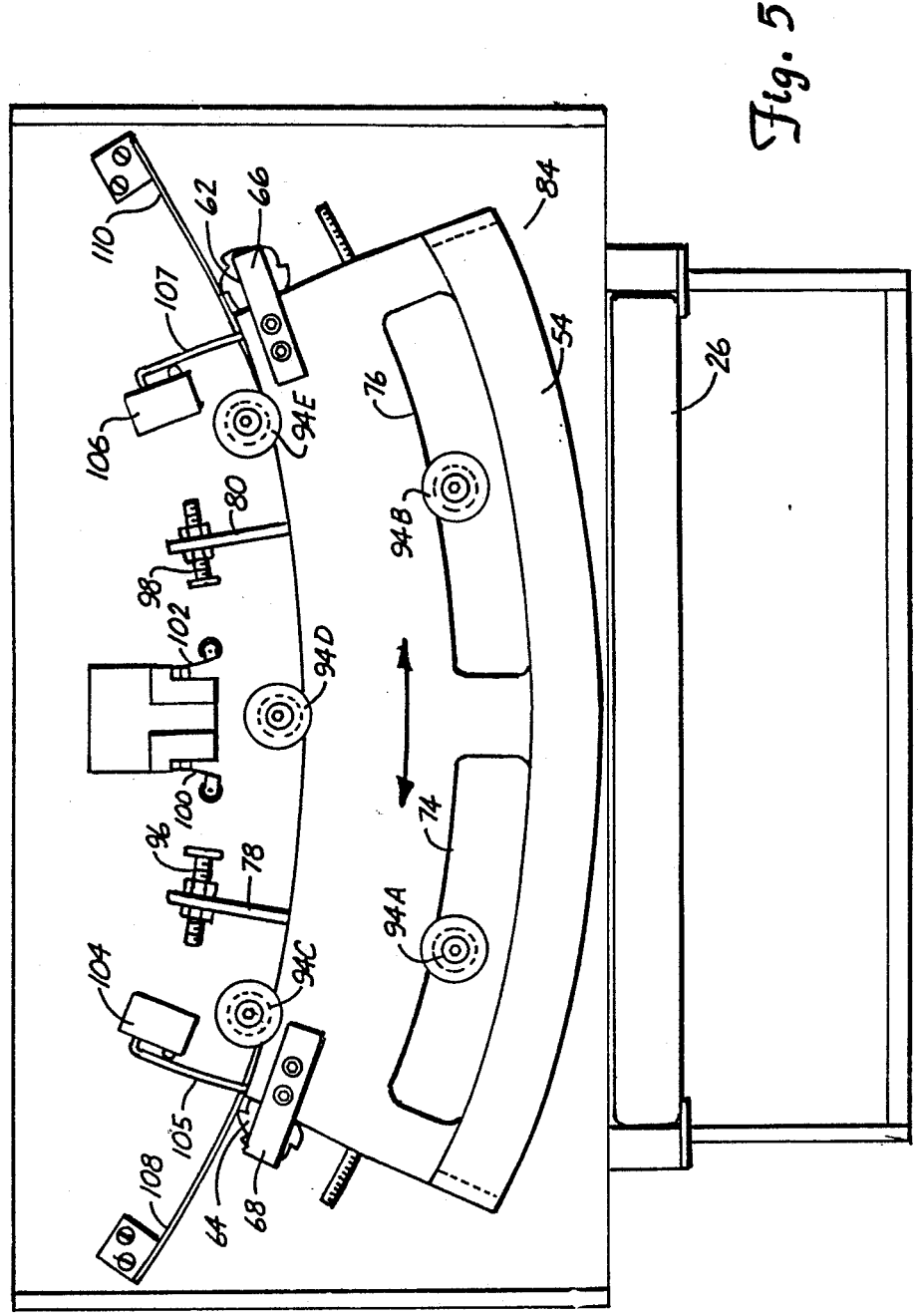

MAMMOGRAPHY APPARATUS

BACKGROUND OF THE INVENTION

1. Field of the Invention.

The invention relates to an x-ray mammography apparatus.

2. Technological Background

Breast cancer is a major cause of death and disability among women in most western countries. Its incidence increases with age. At age 40, the incidence of invasive breast carcinoma is about 80 cases per 100,000 women. At the age of 50, the rate increases to 180 cases per 100,000 women. At the age of 60, the rate is about 240 cases per year per 100,000 women. In all, one out of eleven women in the United States develop breast cancer in their lifetime, the vast majority of cases occurring in the middle and later years of life. Accordingly, annual mammography examination becomes a part of many women's lives above the age of 35 to 40.

Mammography is x-ray examination of a woman's breasts to detect the presence of potentially cancerous tumors. Dr. Ingvar Andersson, writing in the bulletin Medical Radiography and Photography, volume 62, number 2, 1986, at page 4, observed that "few radiographic examinations are as sensitive to improper technique as mammography." Mammography involves imaging structures that have small differences in x-ray radiation absorption characteristics. Successful mammography requires dedicated x-ray apparatus be used for examination. Special, highly monochromatic x-ray sources and good beam filtration are required. Breast compression is is used to reduce scatter by decreasing the thickness of the breast and to separate the layers of tissue. Meticulous film processing is done to obtain the maximum possible image contrast. Nevertheless, mammography requires large radiation dosages when compared to conventional chest x-rays. A conventional posterior/anterior (P/A) chest x-ray examination results in a radiation dosage of 30 millirads, a mammogram examination for a woman with breasts of average size and density involves a dosage of about 1000 millirads, a factor of increase of over 30.

Mammography presently offers the most sensitive technique for early diagnosis of cancerous growths, including the potential for demonstrating non-palpable cancer and precancerous growths. Early detection, when the tumor is small, offers the best prognosis for the cancer patient.

However, the potential adverse effects of x-ray mammograpy, particularly the relationship of annual x-ray examination of women's breasts with possible induced cancers in breast tissue, poses a dilemma to treating physicians. An increased incidence of breast cancer has been observed among women subjected to ionizing radiation below the age of 30 at the time of exposure. Epidemiologic data relating to the carcinogenic effect of exposing breasts to ionizing radiation suggests, at high dose levels, a linear relationship of increasing cancer risk per rad per year of radiation received. While linear extrapolation of such data to dosage rates commonly associated with mammography (typically on the order 1000 millirads per examination with state of the art equipment) is not necessarily valid, the increased incidence rates suggest that a number of cancers per year can be anticipated from this examination process. Physicians, thus, are compelled to balance the risks of missing detection of an early cancer with the risk of inducing cancer in an otherwise healthy person when they recommend a schedule of mammography examinations.

The critical parameters relating radiation dosages to cancer incidence rates suggested by the epidemiological data are, (1) dosage per examination, and (2) cumulative radiation received by the patient. Reduction of radiation exposure per examination promises a number of benefits. Among these would be the ability to maintain a schedule of examinations reasonably calculated to detect early cancers with a reduced risk of induced cancer from each examination and a reduced risk of induced cancer from the cumulative dosage over the lifetime of a woman.

The low difference in x-ray absorption characteristics between cancerous and noncancerous tissue has made mammography particularly susceptible to imaging problems caused by scattered radiation. Scattered radiation is secondary radiation produced in the radiated breast, and emanating in all directions. According to some studies, scattered radiation may amount to up to 80% of the total radiation exposing the film in a mammogram, resulting in image deterioration and fogging by loss of contrast. This means that imaging of the areas of the breast is done with only about 20% of the radiation exposing the film. Improvement of the ratio can be effected using techniques for suppression of scattered radiation.

Bucky grids are positioned between an object being x-rayed and film being exposed to the x-rays to prevent secondary radiation from reaching the film and thereby improve image contrast on the film. They also reduce primary radiation reaching the film, which in turn may require a compensating increase in radiation exposure of the breast. A Bucky grid typically includes thin strips of x-ray radiation absorbing material, called lamellae, substantially aligned with the incident course of the radiation from the x-ray source, with x-rays transmitted through the gaps between the lamellae. Only a portion of the x-ray radiation substantially aligned with radiation emitted from the x-ray source is transmitted through the gaps in the grid. The degree of alignment required is a function of the ratio of the height of the lamellae to the width of the gaps between lamellae. Radiation not aligned with radiation from the source is blocked by the grid from reaching the film. The proportion of aligned x-ray radiation transmitted through the grid is a function of the ratio of the thickness of the lamellae to the width of the gaps between the lamellae, the absorption characteristics of the interspace material and, in current Bucky grids, the precision of the focusing of the grid.

Bucky grids used in mammography have come as either stationary flat grids, or reciprocating flat grids. A stationary Bucky grid will cast a shadow where the image is formed, unless the grid is composed of extremely fine lamellae (on the order of 80 lines per centimeter). A grid which is reciprocated tangentially through an x-ray beam during exposure blurs the shadow cast by the grid. It is a rule of thumb that a minimum of 15 to 20 lamellae should pass each exposed point of a film to effectively blur the shadow of the lamellea regardless of the duration of the exposure.

The employment of bucky grids incorporating extremely fine lamellae and short grid travels has been driven in part by the requirements of imaging as much of the juxtathoracic portion of the breast as possible.

Two favored views used to insude reasonably complete imaging of the breast are the so called "oblique" and "lateral" views. A compact bucky grid aids in positioning the woman undergoing examination. Flat grids with tightly packed lamellae traveling over a short distance have been employed for ease of positioning against the breast, particularly for oblique views of the breast. Thus designers of both stationary and reciprocating grids have repeatedly reduced lamellae width.

Stationary grids used in mammography are extremely shallow (about 1 mm in height) and have densely packed lamellae. The height to width ratio of the gap between lamellae is usually about 3.5:1. Reciprocating grids generally have a height to width gap ratio of 5:1. Dedicated mammography machines of either type have used a flat grid with reinforcing spacing material between lamellae. Focus of the grid is the extent to which the lamellae are aligned with radiation from the source. If the grid is a reciprocating grid, maximum focus occurs only at the center point of the grid's travel. Thus, only at the center point the grid's travel is the theoretical maximum amount of direct radiation passing through the grid. As the grid becomes noncentered, the lamellae move off center and progressively larger proportions of useful radiation are absorbed.

Mammography machines, employing reciprocating, flat Bucky grids, have focused on reducing the thickness of the lamellae and the width of the interstitial gaps to a minimum to provide minimum offset of the grid during operation. The relationship between the gaps and the shadows cast by the lamellae is called the open area. In an ideal Bucky grid, it may be 60% at 28 kv in the center position. Because the grids move off center during operation and due to mechanical imperfections in the mammography grids, the effective open area can be reduced to as low as 37% at the same energy setting in the maximum off center position. By increasing the number of lamellae per given unit of length, the degree to which the noncentered lamellae are out of alignment with respect to the x-ray source is reduced. In stationary grids, lamellae have been made continuously thinner and more closely packed to eliminate the shadow problem. However, for any given material, such as lead, tantalum, tungsten, or any other heavy metal, there is a minimum thickness below which the material becomes inefficient at absorbing x-ray radiation. Thus, as the number of lamellae per unit length is increased, the total area of lead absorbing material presented to the x-ray source as a proportion of the area of the grid increases, reducing direct transmission of x-ray radiation and thereby requiring an increase in exposure to the breast.

Bucky grids with high ratios of lamellae height to gap width reduce transmission of scatter and secondary radiation through the Bucky grid. However, the focus problem of flat grids in mammography limits the lamellae height to gap width ratio to about 5:1, and in some cases has forced utilization of ratios as low as 2:1. These low ratios result in excessive scatter radiation being passed by the Bucky grids, lowering the quality of the image. Mammography grids, having extremely thin lamellae requiring support to retain shape are inefficient in x-ray primary radiation transmission.

SUMMARY OF THE INVENTION

The mammography apparatus of the present invention provides a substantial reduction in radiation exposure per mammography examination when employed with common, present day x-ray sources. In addition, there occurs improved image contrast between areas of marginal x-ray absorption differences.

A conventional x-ray source, of a type typically employed to generate x-ray radiation of energies suitable for exposure of soft tissues, is used to expose a woman's breast to incident x-ray radiation. The woman's breast is compressed between extremely thin, low mass upper and lower polymeric compression plates, which generate substantially no secondary radiation. A reciprocating, slot grid formed on a cylindrical section is provided directly beneath the lower compression plate, preventing transmission of scattered radiation generated in the breast. The lamellae of the slot grid cast shadows on a film/screen cannister which are blurred by the movement of the grid. Stiration effects resulting from an uneven shadow density are avoided by not permitting the lamellae shadow to overlap at the points near the respective ends of the travel where the x-ray source is turned on and off.

Unlike earlier Bucky grids designed for use in mammography, the reciprocating, slot grid has at least a 90% open area at all positions of its travel to transmission of directly incident x-ray radiation (i.e. radiation perpendicular to the tangent of the direction of travel of the grid at the point of incidence). X-ray transmitting slots are formed between x-ray absorbing lamellae, which extend radially in directions from an axis through the x-ray source. The slots between lamellae of the grid are open air slots to reduce x-ray absorption. At least a 7:1 ratio between lamellae height to open air gap width is used to minimize transmission of scattered x-ray radiation through the grid, enhancing image quality.

The large height to gap ratio is obtainable in part by use of a radially aligned lamellae, which substantially eliminates grid focus problems. Thus, maximum aligned x-ray transmission is achieved at all points of the grid's travel. A low density of lamellae in the grid, typically on the order of 3 to 6 lamellae per cm, reduces the need for exceptionally close tolerances in manufacturing and permits use lamellae of sufficient width such as to be substantially self-supporting.

BRIEF DESCRIPTION OF THE DRAWINGS

FIG. 4 is a front view of the mammography apparatus indicating the position of the Bucky scatter grid in its housing.

FIG. 5 is a frontal view of the Bucky grid assembly depicting mounting of the assembly on its travel.

DETAILED DESCRIPTION OF THE PREFERRED EMBODIMENT

Figure 1:
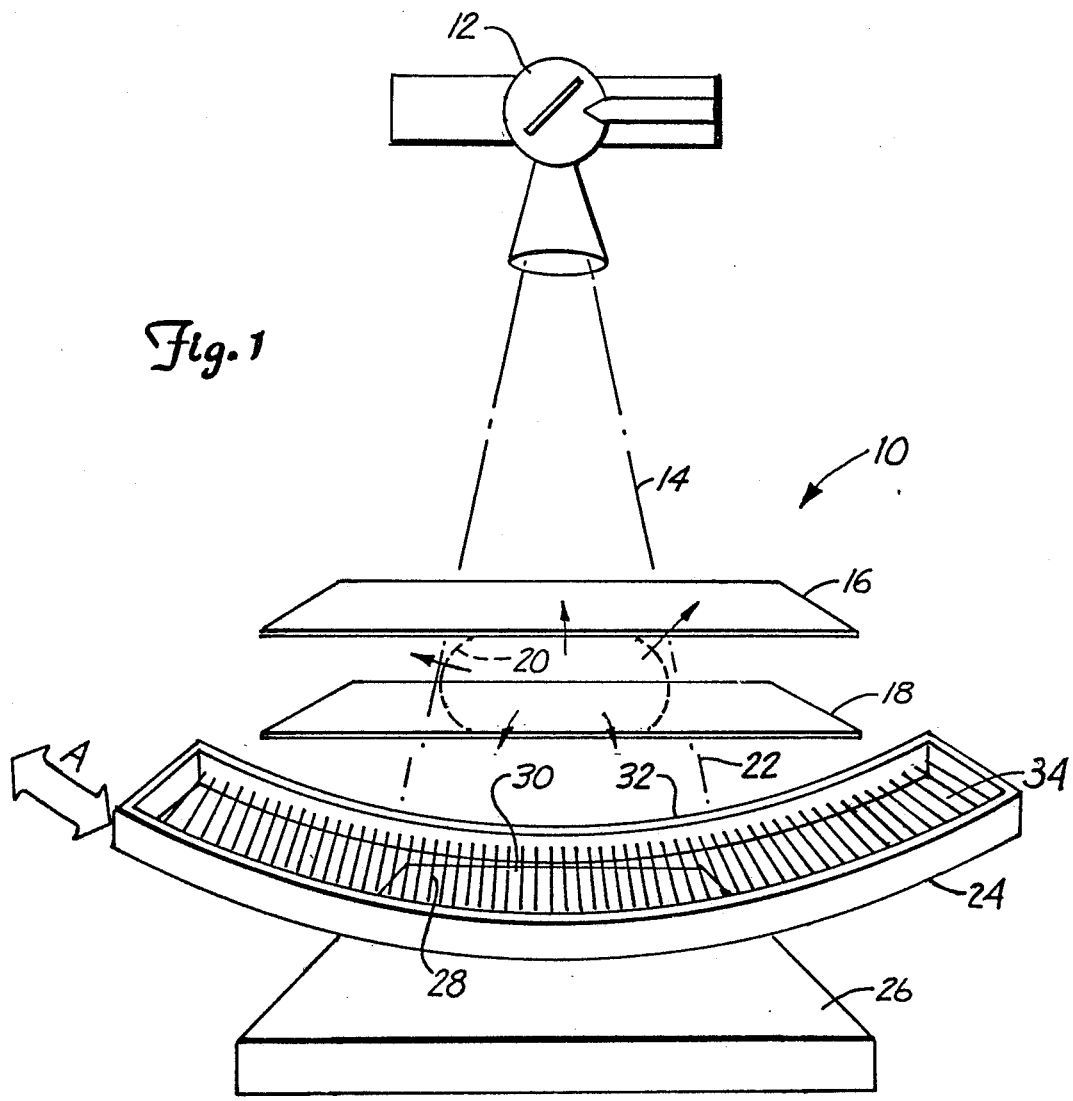
FIG. 1 is a schematic of the arrangement of the functional components of the present mammography apparatus.

FIG. 1 illustrates a schematic arrangement of a mammography apparatus 10. A highly monochromatic x-ray source 12 emits a cone-shaped x-ray beam 14 towards mammography apparatus 10. Compressed between upper compression plate 16 and lower compression plate 18 is a woman's breast 20, shown in hatching, where it is exposed to the incident x-ray beam 14. X-ray beam 14 is shaped by an operator as required to fully illuminate a woman's breast 20, but no more. Scattered x-rays from breast 20 are indicated by arrows 22. Compression plates 16 and 18 are formed from 3 mils thick polyester sheets, generate little secondary radiation and exhibit negligible scattering of radiation. A reciprocating slot grid 24 is disposed between compression plate 18 and a film/screen cassette 26 for preventing transmission of scattered x-ray radiation to the film/screen cassette. Slot grid 24 and film/screen cassette 26 are positioned closely to lower compression plate 18 to minimize magnification effects.

Slot grid 24 is formed on a cylindrical section centered on an axis through x-radiation source 12. Slot grid 24 has a reciprocating travel indicating by double headed arrow "A". A plurality of x-ray radiation absorbing lamellae 28 are disposed in slot grid 24, extending radially from an axis through x-radiation source 12. Lamellae 28 are typically lead strips of between 0.075 mm and 0.25 mm thickness, evenly spaced along the slot grid 24 at a density of 3-6 strips per cm of grid 24. Between each pair of adjacent lamellae 28 is an air gap or slot 30. The ratio of the height of each slot 30 (i.e. the height of lamellae 28) to its width (i.e. the distance between the lamellae) is a minimum of 7:1 and is potentially as large as 15:1. Lamellae 28 themselves can have a height of 3 to 20 mm. The high slot height to width ratio and high absolute height of the lamellae result in substantially improved scattered radiation suppression and in noticeably improved image quality and contrast. The top and bottom of grid 24 are enclosed by thin polymeric sheets 32 and 34, preferably of between 0.025 and 0.127 mm thickness, but no more than 0.17 mm thickness applied to the grid with a layer of adhesive to hold the lamellae in place.

Figure 2:
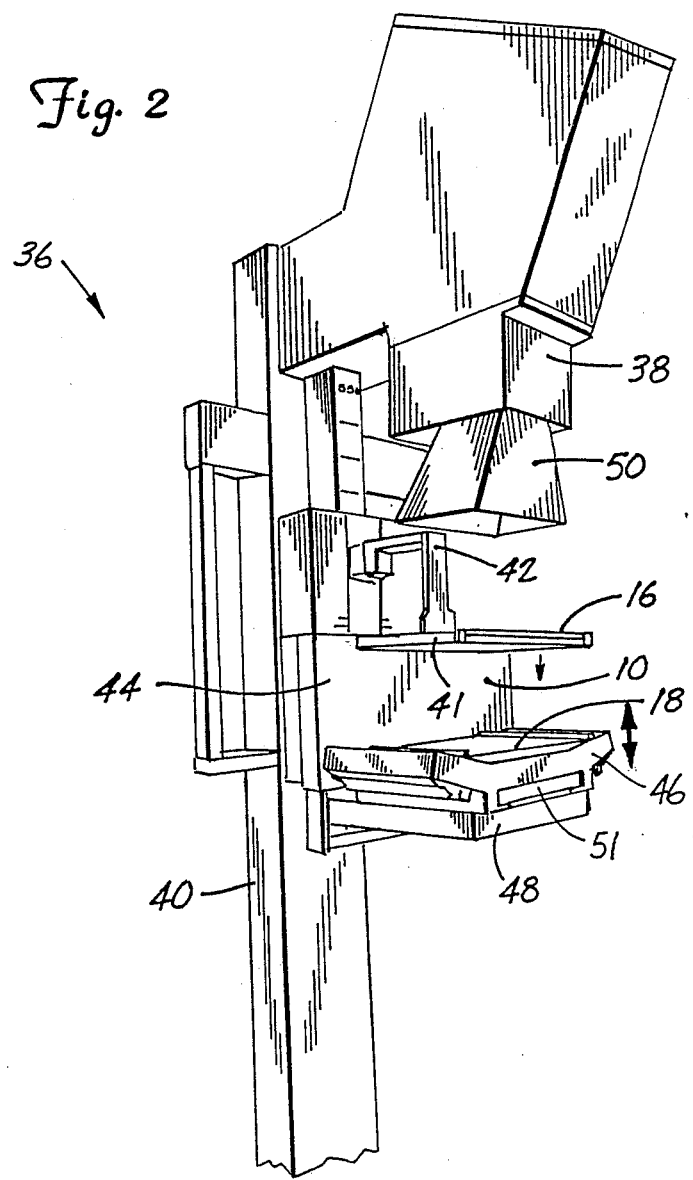
FIG. 2 is a perspective view of the mammography apparatus of the present invention.

FIG. 2 illustrates mammography apparatus 10 retrofitted to a prior art mammography x-ray radiation generator 36. Mammography apparatus 10, and x-ray source housing 38, are vertically positionable on generator 36 to allow convenient allow position adjustment of the apparatus for women of different height. In addition, mammography apparatus 10 and x-ray radiation source housing 38 are rotatable on an axis perpendicular to stand 40 in order to allow presentation of a breast for generation of images of oblique views. Upper compression plate 16 is mounted in a frame 41 positioned on arm 42, which extends forward from mounting adaptor 44, allowing vertical adjustment of the compression plate relative to lower compression plate 18 and grid housing 46.

Grid housing 46 contains slot grid 24 and a travel mechanism for reciprocating the grid (described below). Grid housing 46 is mounted to and extends forward from mounting adaptor 44. Also attached to mounting adaptor 44 is support 48 which is disposed immediately below grid housing 46.

X-ray radiation source housing 38 houses x-ray source 12, which emits a beam of x-ray radiation from opening 50. The emitted beam has a rectangular section and is directed to illuminate a film/screen cassette positioned in a tray 51 disposed in the lower portion of grid housing 46. The examinee's breast is exposed to x-ray radiation as close to the chest wall as possible. A source of visible light is housed in x-ray source housing 38, behind the x-ray source, for illuminating a target area substantially coincident with the area illuminated by an emitted x-ray beam. Using the visible light source the radiologist or technician can appropriately position the breast and limit the area covered before x-ray exposure to define an x-ray beam cover substantially all of the breast and little else.

Figure 3:
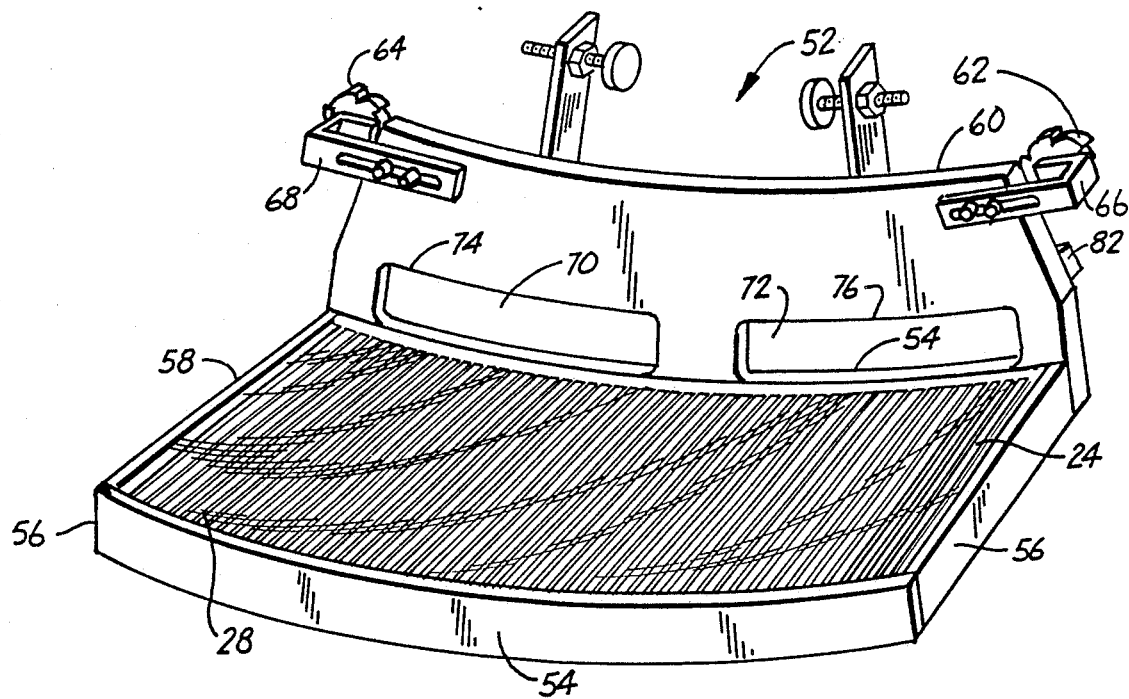
FIG. 3 is a perspective view of a Bucky scatter grid.

FIG. 3 illustrates a preferred slot grid assembly 52 including cylindrical section grid 24. Cylindrical section grid 24 preferably has a lamellae density of 3-6 x-ray absorbing strips per cm. At a lamellae thickness of 0.025 cm and three strips per cm, an air spaced slot grid with an open area of about 93% is provided. Many prior art mammography apparatuses have an open area of only about 50% to 60%, and, slot grid 24 achieves a substantial improvement in radiation transmission efficiency. Lamellae 28 are set into front and rear side pieces 54 and 54' of grid frame 56, disposed substantially parallel to one another and end pieces 58 of frame 56. Side pieces 54 are bent along the circumference of the desired cylindrical section for grid 24 with individual lamellae 28 set in frame 56 extending radially from the longitudinal axis of the cylindrical section.

Grid frame 56 is attached to a support plate 60 along rear side piece 54'. Support plate 60 allows mounting of grid assembly 52 to a movement described below. Support plate 60 accordingly includes additional members adapted to engage and cooperate with the travel. Step gears 62 and 64 extend from each end of support plate 60 on extension brackets 66 and 68, respectively. Openings 70 and 72 in support plate 60 have upper edges 74 and 76, respectively, which have a curvature centered on the same axis as to the curvature of side pieces 54 and 54'. Openings 70 and 72 are sized to admit support rollers (shown in FIG. 4), which engage support plate 60 under edges 74 and 76. A pair of switch engaging arms 78 and 80 are visible extending vertically from behind support plate 60. Arms 78 and 60 are supported from a rearward extending flange 82 attached to the backside of support plate 60.

Figure 6:
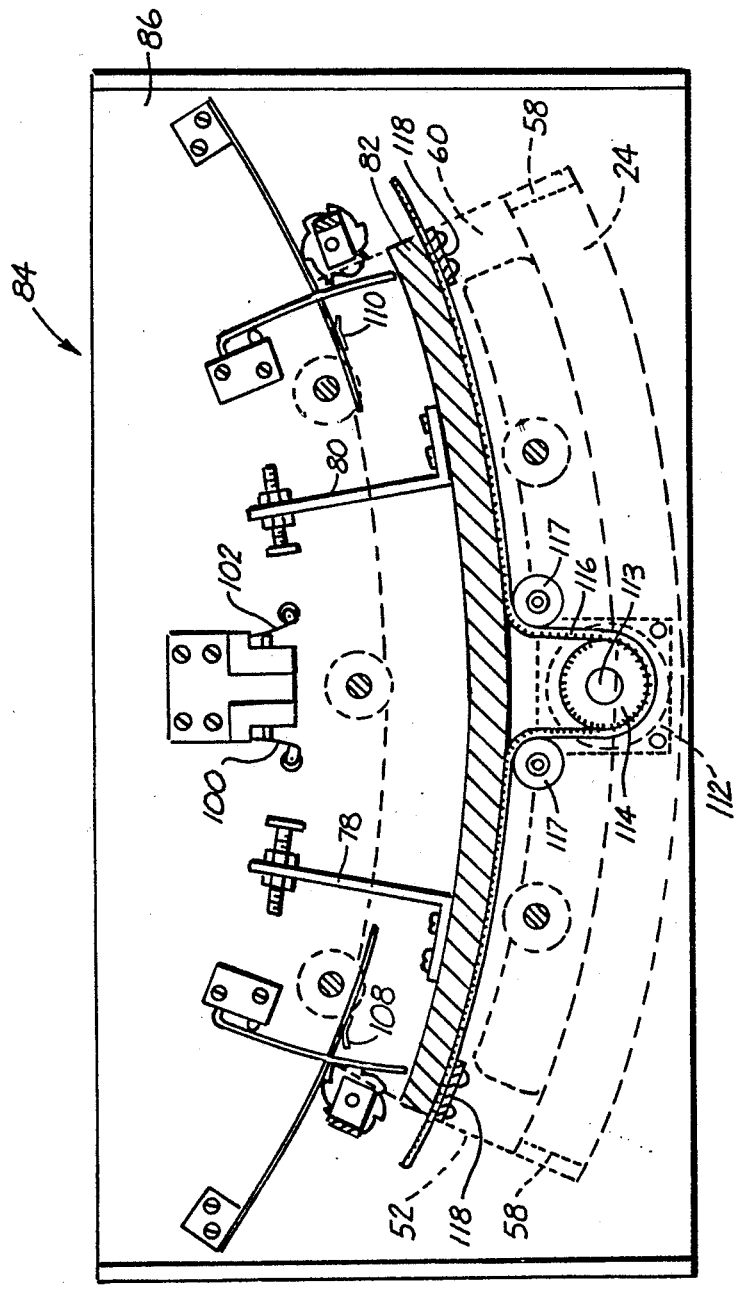
FIG. 6 is a cross sectional view of the reciprocating mechanism for the Bucky scatter grid.

FIGS. 4 through 6 illustrate the positioning of grid assembly 52 in grid housing 46 and the mating of the grid assembly 52 with grid movement 84 (FIG. 6). In FIG. 4, the disposition of grid housing 46 indicates the alignment of slot grid 24 with upper and lower compression plates 16 and 18 and film/screen cassette 26 in housing 48. Lower compression plate 18 is attached to tensioning members 86 and 88 which extend around the ends of grid housing 46 and are tightened by a plurality of screws 90 which extend through the members into receptacles extending from the housing. Grid assembly 24 has a travel extending in line with its curvature in both directions around its central axis, as indicated by the arrows. Lamellae 28 are again seen to extend radially from the central axis of the cylindrical section of slot grid 24, an orientation which is preserved by virtue of the cylindrical shape of the grid and the circular motion of the grid.

FIG. 5 illustrates grid assembly 52 mated with movement 84 for providing reciprocating motion of the grid assembly along a circular path. Back plane 86 supports rollers 94A-94E, of which 94A and 94B are positioned under edges 74 and 76 supporting back support plate 60 and 94C-94E ride against the upper edge of the support plate to prevent tipping of the support plate on the supporting rollers.

Arms 78 and 80 include position adjustable switch actuators 96 and 98, respectively. Switch actuators 96 and 98 are carried by back support plate 60 against grid travel reversing switches 100 and 102, respectively, during operation of slot grid 24. Each time one of switches 100 or 102 is hit, the slot grid reverses its direction of travel, reciprocating back and forth between extreme points in the travel determined by the adjustment of switch actuators 96 and 98.

If the x-ray source is left on during reversal of grid travel, a shadow will be cast by grid 24 on film/screen cassette 26, compromising the quality of the reproduced image. Step gears 62 and 64 each carry cam actuators (shown in FIG. 7) for actuating x-ray disable switches 104 and 106. During reversal of travel of grid assembly 60, slot grid 24 will momentarily come to a halt. Thus, x-ray source 12 is turned off during reversal the direction of grid assembly 60. Appropriate timing of disablement and reenablement of x-ray source 12 during reciprocation of slot grid 24 helps prevent formation of striation artifacts in the image. Ideally each succeeding disablement and reenablement of the x-ray sources, during a given exposure, will occur at a point where the shadow of lamellae 28 are not superimposed over the shadow of other lamellae from a previous disablement or re-enablement. In other words, a better exposure is one in which the exposure of all parts of the film is closest to the same, i.e. a homogeneous exposure.

Superimposition of shadows is substantially avoided by inclusion of step gears 62 and 64, which are advanced by hooks 110 and 108, respectively, which are mounted on back plane 86. Once each cycle of grid assembly 60 in its travel hooks 108 and 110 will engage and rotate, by one step, step gears 62 and 64. Actuation arms 105 and 107 of x-ray disable switches 104 and 106 are engaged by the cams at a different point in the travel each cycle. Staggered disablement and reenablement of the x-ray source aids in avoiding casting of a heavier shadow by lamellae 28 over any particular portion of film/screen 26. Alternatively, as described with reference to FIG. 8B below, uneven exposure density is avoided by providing turn on and turn off of the x-ray source at precisely defined grid positions, selected to avoid overlays of lamellae by turning the source on and off at points where individual lamellae are positioned to abut, but not overlap, the location of the lamellae at the beginning of the cycle.

FIG. .6 illustrates the prime mover of grid assembly 60. Motor 112 is mounted behind back plane 86 with a shaft 113 extending through the back plane supporting a timing gear 114 for rotation. Timing belt 116 is partially wrapped around timing gear 114, held in position by pulleys 117. Timing belt 116 is rigidly connected to rearward extending flange 82. Rotation of shaft 113 results in lateral displacement of grid assembly 60, the direction of displacement reversing with each reversal of direction of rotation of motor 112.

Figure 7:
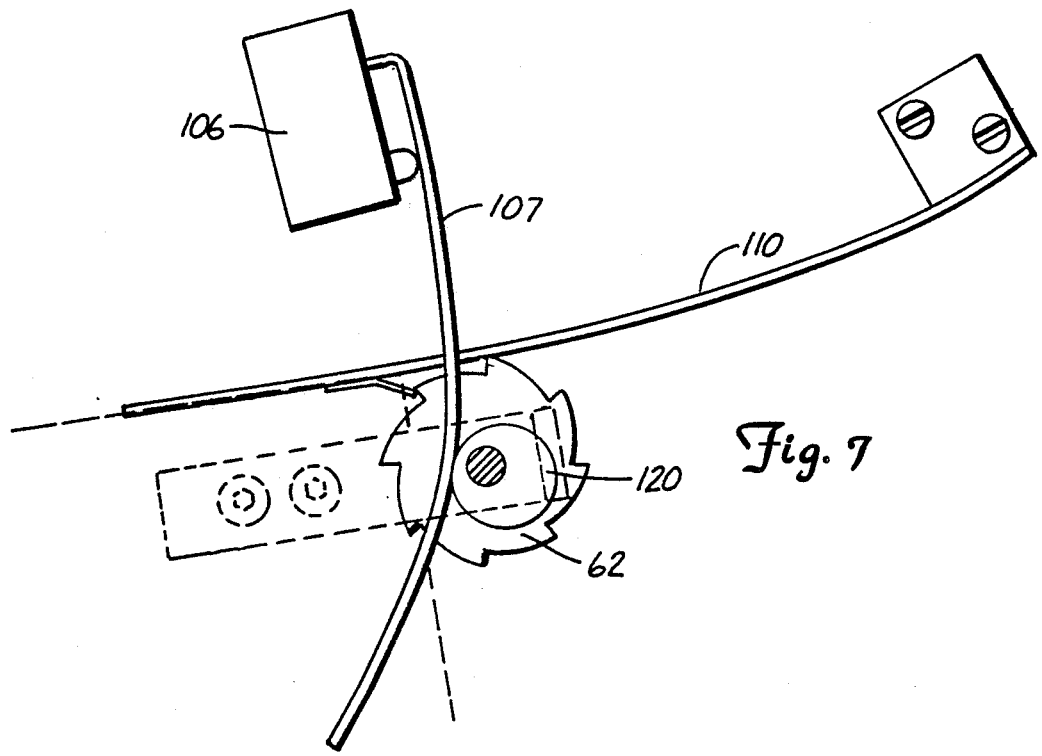
FIG. 7 is a detail view of a cam actuator for the x-ray source.

FIG. 7 illustrates mechanical aspects of a staggered x-ray disable mechanism. X-ray disable switch 106 is actuated by depression of actuating arm 107 into the switch. Actuating arm 107, during disablement of the x-ray source, abuts against cam 120 which is mounted for rotation with step gear 62. As set forth above, step gear 62 is rotated a step once each complete cycle in the travel of gear assembly 60 by hook 110. Because cam 120 and step gear 62 are fixed for rotation at a fixed location with respect to gear assembly 60, the nonconcentric aspect of the cam results in the x-ray source being disabled at a different point during reversal of the travel with each cycle.

It will be apparent to those skilled in the art that the electromechanical actuation of travel reversal and x-ray source disablement staggering can also be conveniently carried out in numerous other ways, including optical detection of position, etc. Such position sensing could be taken from shaft 113 or directly from grid assembly 60.

Figure 8A:
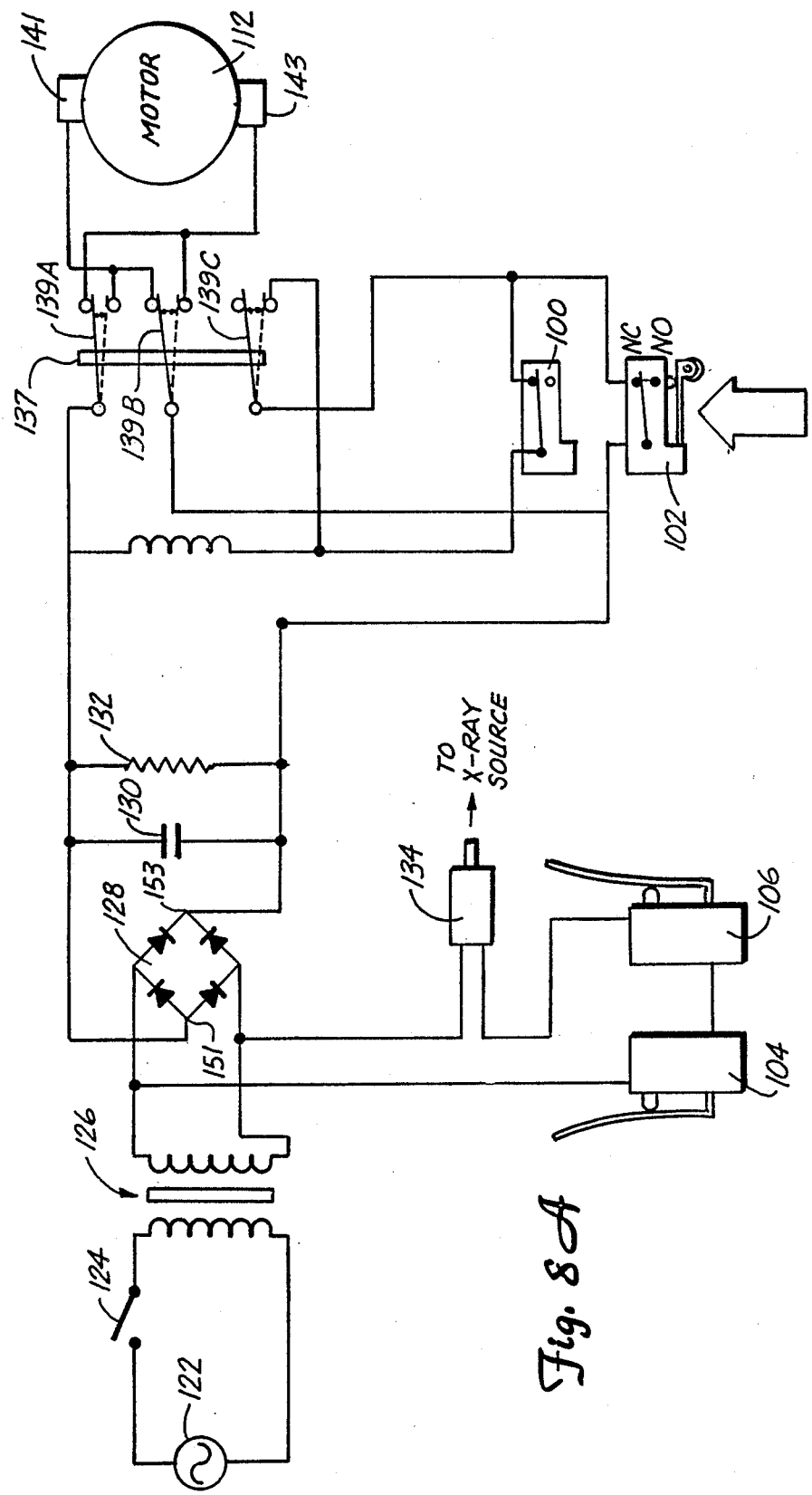
FIG. 8 is a circuit schematic for a drive mechanism for the grid.
Figure 8B:
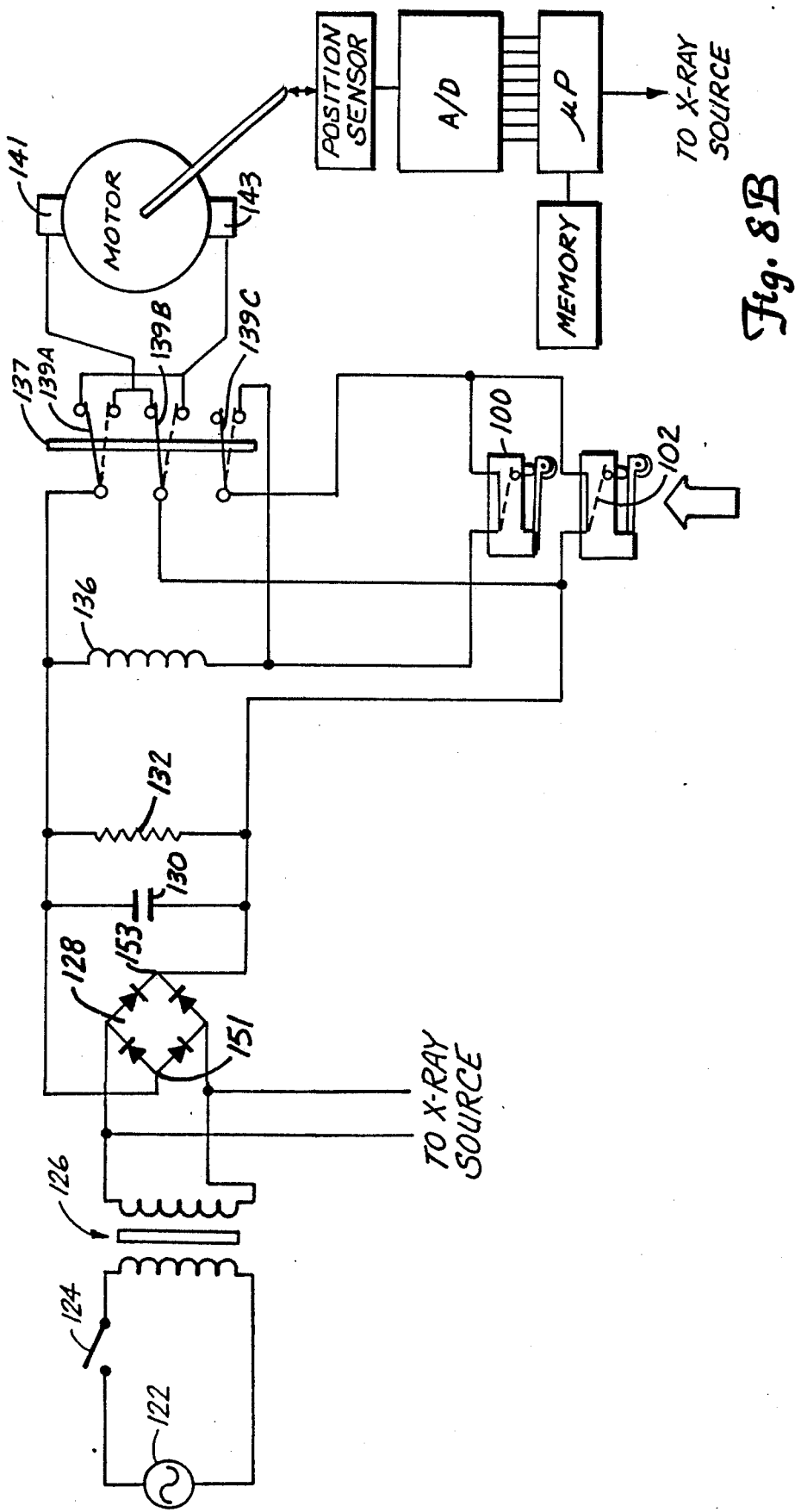

FIG. 8A illustrates in a mixed circuit and mechanical element schematic an electro-mechanically actuated prime mover and x-ray disablement circuit. A conventional A.C. power source 122 provides power to operate an x-ray source and reciprocating slot grid assembly 60. A.C. power is applied across the primary winding of a step up transformer 126 by a switch 124. Power is transmitted from across the secondary winding to conventional x-ray source circuitry (not shown) by disable switches 104 and 106 and relay 134. Relay 134 is manually actuated to turn the x-ray source on and off. Switches 104 and 106 are normally closed, but can be opened as described above for preventing x-ray source operation during reversal of the travel of slot grid assembly Closure of switch 124 turns motor 112 on. The output of the secondary winding of transformer 126 is rectified by diode bridge 128 to provide D.C. current for the motor. The D.C. output of bridge 128 is filtered by capacitor 130. Resistor 132 discharges capacitor 130 at such time as switch 124 is opened. Solenoid coil 136 positions an armature 137 on which relay switches 139A, 139B and 139C are positioned. The position of switches 139A and 139B determines the polarity applied to motor input terminals 141 and 143 and across motor 112 for controlling the direction of rotation of the motor.

Mechanical actuation of grid direction reversing switches 100 and 102 controls solenoid 136. Switches 100 and 102 are normally closed in the completing of the circuit as shown in the figure. Grid assembly 60 makes contact with and opens switches 102 and 104, in alternation, at the opposite extremes of its reciprocating motion.

Initially a current is established in solenoid 136 from terminal 153, through switch 102, switch 100 and solenoid 136 to terminal 151. Switches 139A–139C are the positions indicated by the solid lines. Impact of the grid assembly with switch 100 interrupts current through solenoid 136 giving rise to a responsive, oppositely directed potential across the solenoid coil. Armature 137 then moves switches 139A–139C to the hatched positions, reversing the polarity applied to motor 112 and providing a new current path from terminal 153 through solenoid 136 to terminal 151. The new current path initially leads from terminal 153, through switch 102 and switch 139C to solenoid coil 136. Interruption of switch 102 opens this path resulting in generation of a potential across solenoid 136 and movement of armature 137 to open switch 139C and change the position of switches 139A and 139B, again reversing motor 112.

Employment of a microprocessor 164 to determine to determine when the x-ray source is turned on and turned off as a function of slot grid position permits greater flexibility of operation of the mammography apparatus. Motor 112 has a shaft 159 whose radial displacement is related to slot grid position. A position sensor 160 develops a signal indicating a shaft 159 displacement. The signal from sensor 160 is converted to a digital signal in analog to digital converter 162 and the digital position signal is coupled to microprocessor 164. Microprocessor 164 has an associated memory 166 which stores data indicating the position of the grid at the ends of the travel, i.e. the position of the grid where it reverses direction. Microprocessor 164 calculates a grid position substantially adjacent the reversal point where the x-ray source is turned on or turned off, depending upon whether the grid is moving toward the closer reversal position or away. With each reversal of the grid, at both ends of the travel, the grid position for turn on and turn off is calculated such that the shadows cast by the lamellae abut, but do not overlay the shadow of the lamellae from the previous change in state of the source. This is done to even out exposure of the mammograph.

Test embodiments of the mammography apparatus of the present invention have, in the appraisal of independent expert consultants, produced images of higher contrast, detail and thus better diagnostic information on test structures than previously known in the art. Improved contrast promises earlier detection of cancerous tumors. These results have been obtained notwithstanding an average reduction in radiation exposure of 40%. For the average-sized woman, this would relate to a reduction in x-ray exposure per examination from 1000 millirads to about 600 millirads. It is expected that such a reduction in radiation exposure will result in decreased incidents of cancer provided by repeated x-ray examination. Over the life of an 80 year old woman, the reduction in cumulative radiation dosage at the current recommended schedule of examinations would be from 36,000 mr to 21,600 mr.

Although the present invention has been described with reference to preferred embodiments, workers skilled in the art will recognize that changes may be made in form and detail without departing from the spirit and scope of the invention.

What is claimed is:

1. A method of performing a mammography examination on a human subject, the method comprising the steps of:
   generating x-rays from an x-ray source;
   exposing an image receptor to x-ray radiation from an x-ray source through a breast of the subject;
   suppressing scattered x-ray radiation produced in the breast relative to the image receptor with a slot grid of circular section centered on an axis through the x-ray source;
   moving the slot grid during the mammography examination to blur areas of negative density cast by the slot grid on the image receptor; and
   initiating and interrupting the generation of x-ray radiation during movement of the slot grid as a function of slot grid position to provide for cumulative homogeneous exposure of the image receptor.

2. The method of claim 1 wherein the step of moving the slot grid includes reciprocation of the slot grid along a circular travel centered on the focus spot of the x-ray source.

3. A radiographic apparatus comprising:
   a source of x-ray radiation;
   the ratio of the height of each of an adjacent pair of lamellae to the width of the respective defined gap being at least 7:1;
   a travel for the slot grid around the axis; and
   an x-ray source actuation controller including:
   means for indicating the position of the slot grid;
   means responsive to the means for indicating the position of the slot grid for enabling the generation of x-ray radiation such that the areas of negative density cast by the lamellae on an image receptor at the moment of interruption of x-ray generation substantially abut, but do not overlap the areas of negative density cast by the lamellae on the image receptor at the moment of initiation of x-ray generation.

4. The grid of claim 3 wherein the lamellae are disposed at a radial density of at least three and no more than six lamellae per cm. at the circumference.

5. The slot grid of claim 4 wherein the thickness of the lamellae is between 0.075 mm and 0.25 mm.

6. The slot grid of claim 5 and further including upper and lower polyester sheets enclosing the lamellae and air gaps, opposing faces of the upper and lower polyester sheets being substantially covered with an adhesive layer for affixing the sheets to the lamellae.

7. A mammography apparatus comprising:
   a source of x-ray radiation;
   a cylindrical section slot grid centered on an axis through the source of x-ray radiation;
   breast compression plates adapted to position a subject's breast between the source of x-ray radiation and the cylindrical section slot grid;
   an image receptor positioned to receive x-rays transmitted through the slot grid;
   the cylindrical section slot grid including a plurality of x-ray radiation absorbing lamellae disposed parallel to and aligned radially from the axis, the lamellae defining an x-ray transmitting air spaced gap between adjacent lamellae;
   a travel for the slot grid centered on the axis;
   a prime mover for moving the slot grid along its travel; and
   an x-ray source actuation controller responsive to the position of the slot grid while moving in its travel to control the periods of x-ray radiation generation to insure a substantially homogeneous cumulative exposure of the image receptor.

8. The mammography apparatus of claim 7 wherein the slot grid further includes at least 3 lamellae per centimeter around the circumference of the cylindrical section and no more than six lamellae per cm.

9. The mammography apparatus of claim 8 wherein the ratio of the height of each of an adjacent pair of lamellae to the width of the respective defined gap is at least 7:1.

10. The mammography apparatus of claim 9 wherein the thickness of the lamellae is between about 0.075 mm and 0.25 mm.

11. The mammography apparatus of claim 7 wherein the slot grid further includes upper and lower polymeric sheets of not greater than 0.17 mm thickness enclosing the lamellae and air gaps, opposing faces of the upper and lower polymeric sheets being substantially covered with an adhesive layer for affixing the sheets to the lamellae.

12. The mammography apparatus of claim 7 and further including a lower breast support plate and an upper breast compression plate, the support plate and the compression plate being formed of polymeric sheets of between 0.025 and 0.127 mm.

* * * * *

UNITED STATES PATENT AND TRADEMARK OFFICE
CERTIFICATE OF CORRECTION

PATENT NO.  : 4,901,335

DATED       : February 13, 1990

INVENTOR(S) : Daniel J. Ferlic

It is certified that error appears in the above-identified patent and that said Letters Patent is hereby corrected as shown below:

Column 9, line 53, delete the period, and insert --by enabling generation of x-ray radiation between sets of points where the areas of negative density cast by lamellae of the slot grid are substantially adjacent to but not overlapping with one another.--

Column 9, line 59, delete "a source of x-ray radiation" and insert the following:
--a source of x-ray radiation;
  a cylindrical section slot grid centered on an axis through the source of x-ray radiation and including a plurality of x-ray radiation absorbing lamellae disposed parallel to and aligned radially from the axis;--

Column 10, line 36, after "travel;" delete "and".

UNITED STATES PATENT AND TRADEMARK OFFICE
CERTIFICATE OF CORRECTION

PATENT NO. : 4,901,335

DATED : February 13, 1990

INVENTOR(S) : Daniel J. Ferlic

It is certified that error appears in the above-identified patent and that said Letters Patent is hereby corrected as shown below:

Column 10, line 41, delete "receptor" and insert the following:

--means for periodically reversing the direction of movement of the slot grid in its travel; and the x-ray source actuation controller including;

> means for indicating the position of the slot grid during movement of the slot grid;
>
> means for limiting generation of x-ray radiation as a function of grid position;
>
> x-ray radiation being limited such that shadows cast by the lamellae on the image receptor at the moment of interruption of the x-ray radiation substantially abut, but do not overlap the shadows cast by the lamellae on the image receptor at the moment of initiation of x-ray generation.--

UNITED STATES PATENT AND TRADEMARK OFFICE
CERTIFICATE OF CORRECTION

PATENT NO. : 4,901,335

DATED : February 13, 1990

INVENTOR(S) : Daniel J. Ferlic

It is certified that error appears in the above-identified patent and that said Letters Patent is hereby corrected as shown below:

but do not overlap the shadows cast by the lamellae on the image receptor at the moment of initiation of X-ray generation.--

Signed and Sealed this

Sixteenth Day of April, 1991

Attest:

HARRY F. MANBECK, JR.

Attesting Officer

Commissioner of Patents and Trademarks